United States Patent
Fiekowsky et al.

(10) Patent No.: US 6,611,767 B1
(45) Date of Patent: *Aug. 26, 2003

(54) SCANNED IMAGE ALIGNMENT SYSTEMS AND METHODS

(75) Inventors: Peter Fiekowsky, Los Altos, CA (US); Dan M. Bartell, San Carlos, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/542,151

(22) Filed: Apr. 4, 2000

Related U.S. Application Data

(63) Continuation of application No. 08/996,737, filed on Dec. 23, 1997, now Pat. No. 6,090,555.
(60) Provisional application No. 60/069,032, filed on Dec. 11, 1997.
(51) Int. Cl.$^7$ .......................... G06F 19/00; G11C 17/00; C12Q 1/68; G06K 9/32; G06K 9/50
(52) U.S. Cl. ................. 702/19; 365/94; 435/6; 382/129; 382/279; 382/287
(58) Field of Search .................... 435/6; 128/653.5; 436/518; 348/420; 702/19; 365/94; 382/129, 279, 287

(56) References Cited

U.S. PATENT DOCUMENTS

| | | | |
|---|---|---|---|
| 5,143,854 A | | 9/1992 | Pirrung et al. ............... 436/518 |
| 5,471,248 A | | 11/1995 | Bhargava et al. ............ 348/420 |
| 5,497,773 A | * | 3/1996 | Kuhara et al. ........... 128/653.5 |
| 5,604,819 A | | 2/1997 | Barnard ....................... 382/151 |
| 5,744,305 A | * | 4/1998 | Fodor et al. .................... 436/6 |
| 5,835,620 A | * | 11/1998 | Kaplan et al. ............... 382/133 |
| 6,090,555 A | | 7/2000 | Fiekowsky et al. ............. 435/6 |

FOREIGN PATENT DOCUMENTS

| | | |
|---|---|---|
| EP | 0 254 644 | 1/1988 |

\* cited by examiner

*Primary Examiner*—John S. Brusca
(74) *Attorney, Agent, or Firm*—Ritter, Lang & Kaplan LLP

(57) ABSTRACT

Systems and methods for aligning scanned images are provided. A pattern is included in the scanned image so that when the image is convolved with a filter, a recognizable pattern is generated in the convolved image. The scanned image may then be aligned according to the position of the recognizable pattern in the convolved image. The filter may also act to remove the portions of the scanned image that do not correspond to the pattern in the scanned image.

23 Claims, 13 Drawing Sheets

SCANNED IMAGE ALIGNMENT SYSTEMS AND METHODS

This is a continuation of application Ser. No. 08/996,737, filed Dec. 23, 1997, now issued as U.S. Pat. No. 6,090,555, which is hereby incorporated by reference and claims the benefit of U.S. Provisional Application No. 60/069,032, filed Dec. 11, 1997.

COPYRIGHT NOTICE

A portion of the disclosure of this patent document contains material that is subject to copyright protection. The copyright owner has no objection to the xerographic reproduction by anyone of the patent document or the patent disclosure in exactly the form it appears in the Patent and Trademark Office patent file or records, but otherwise reserves all copyright rights whatsoever.

SOFTWARE APPENDICES

A Software Appendix of source code for an embodiment of the invention including two (2) sheets is included herewith.

BACKGROUND OF THE INVENTION

The present invention relates to the field of image processing. More specifically, the present invention relates to computer systems for aligning grids on a scanned image of a chip including hybridized nucleic acid sequences.

Devices and computer systems for forming and using arrays of materials on a chip or substrate are known. For example, PCT applications WO92/10588 and 95/11995, both incorporated herein by reference for all purposes, describe techniques for sequencing or sequence checking nucleic acids and other materials. Arrays for performing these operations may be formed in arrays according to the methods of, for example, the pioneering techniques disclosed in U.S. Pat. Nos. 5,445,934, 5,384,261 and 5,571,639, each incorporated herein by reference for all purposes.

According to one aspect of the techniques described therein, an array of nucleic acid probes is fabricated at known locations on a chip. A labeled nucleic acid is then brought into contact with the chip and a scanner generates an image file (also called a cell file) indicating the locations where the labeled nucleic acids are bound to the chip. Based upon the image file and identities of the probes at specific locations, it becomes possible to extract information such as the nucleotide or monomer sequence of DNA or RNA. Such systems have been used to form, for example, arrays of DNA that may be used to study and detect mutations relevant to genetic diseases, cancers, infectious diseases, HIV, and other genetic characteristics.

The VLSIPS™ technology provides methods of making very large arrays of oligonucleotide probes on very small chips. See U.S. Pat. No. 5,143,854 and PCT patent publication Nos. WO 90/15070 and 92/10092, each of which is incorporated by reference for all purposes. The oligonucleotide probes on the DNA probe array are used to detect complementary nucleic acid sequences in a sample nucleic acid of interest (the "target" nucleic acid).

For sequence checking applications, the chip may be tiled for a specific target nucleic acid sequence. As an example, the chip may contain probes that are perfectly complementary to the target sequence and probes that differ from the target sequence by a single base mismatch. For de novo sequencing applications, the chip may include all the possible probes of a specific length. The probes are tiled on a chip in rows and columns of cells, where each cell includes multiple copies of a particular probe. Additionally, "blank" cells may be present on the chip which do not include any probes. As the blank cells contain no probes, labeled targets should not bind specifically to the chip in this area. Thus, a blank cell provides a measure of the background intensity.

In the scanned image file, a cell is typically represented by multiple pixels. Although a visual inspection of the scanned image file may be performed to identify the individual cells in the scanned image file. It would be desirable to utilize computer-implemented image processing techniques to align the scanned image file.

SUMMARY OF THE INVENTION

Embodiments of the present invention provide innovative techniques for aligning scanned images. A pattern is included in the scanned image so that when the image is convolved with a filter, a recognizable pattern is generated in the convolved image. The scanned image may then be aligned according to the position of the recognizable pattern in the convolved image. The filter may also act to remove or "filter out" the portions of the scanned image that do not correspond to the pattern in the scanned image. Several embodiments of the invention are described below.

In one embodiment, the invention provides a computer-implemented method of aligning scanned images. The scanned image is convolved with a filter. The scanned image includes a first pattern that the filter will convolve into a second pattern in the convolved image. The scanned image is then aligned according to the position of the second pattern in the convolved image. In a preferred embodiment, the first pattern may be a checkerboard pattern that is convolved into a grid pattern in the convolved image.

In another embodiment, the invention provides a method of aligning scanned images of chips with hybridized nucleic sequences. A chip having attached nucleic acid sequences (probes) is synthesized, with the chip including a first pattern of nucleic acid sequences. Labeled nucleic acid sequences are hybridized to nucleic acid sequences on the chip and the hybridized chip is scanned to produce a scanned image. The scanned image is convolved with a filter that will convolve the first pattern into a second pattern in the convolved image. The scanned image is then aligned according to the position of the second pattern in the convolved image. In a preferred embodiment, the first pattern may be a checkerboard pattern that is generated by control nucleic acid sequences that hybridize to alternating squares in the checkerboard pattern.

Other features and advantages of the invention will become readily apparent upon review of the following detailed description in association with the accompanying drawings.

DETAILED DESCRIPTION OF PREFERRED EMBODIMENTS

Overview

In the description that follows, the present invention will be described in reference to preferred embodiments that utilize VLSIPS™ technology for making very large arrays of oligonucleotide probes on chips. However, the invention is not limited to images produced in this fashion and may be advantageously applied other hybridization technologies or images in other technology areas. Therefore, the description of the embodiments that follows for purposes of illustration and not limitation.

Figure 1:
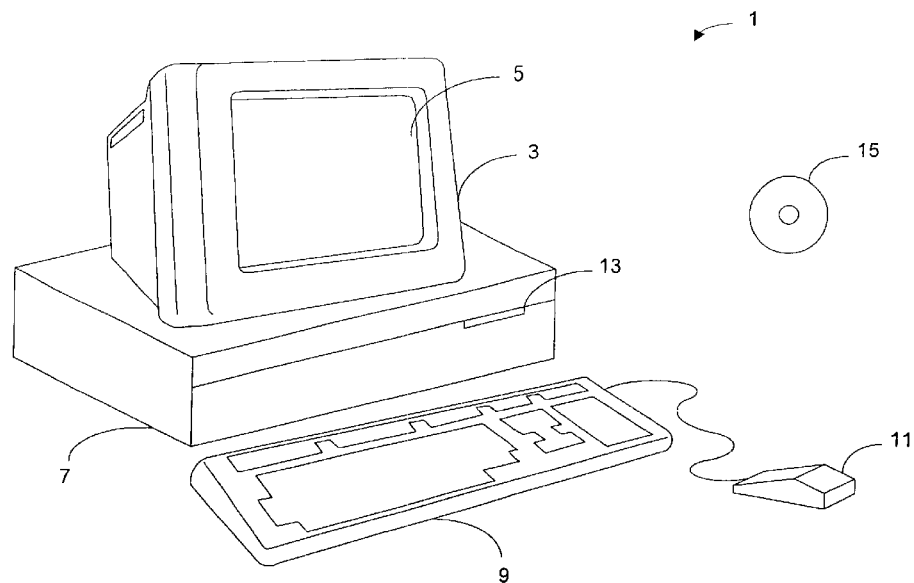
FIG. 1 illustrates an example of a computer system that may be utilized to execute the software of an embodiment of the invention.

FIG. 1 illustrates an example of a computer system that may be used to execute the software of an embodiment of the invention. FIG. 1 shows a computer system 1 that includes a display 3, screen 5, cabinet 7, keyboard 9, and mouse 11. Mouse 11 may have one or more buttons for interacting with a graphical user interface. Cabinet 7 houses a CD-ROM drive 13, system memory and a hard drive (see FIG. 2) which may be utilized to store and retrieve software programs incorporating computer code that implements the invention, data for use with the invention, and the like. Although a CD-ROM 15 is shown as an exemplary computer readable storage medium, other computer readable storage media including floppy disk, tape, flash memory, system memory, and hard drive may be utilized. Additionally, a data signal embodied in a carrier wave (e.g., in a network including the Internet) may be the computer readable storage medium.

Figure 2:
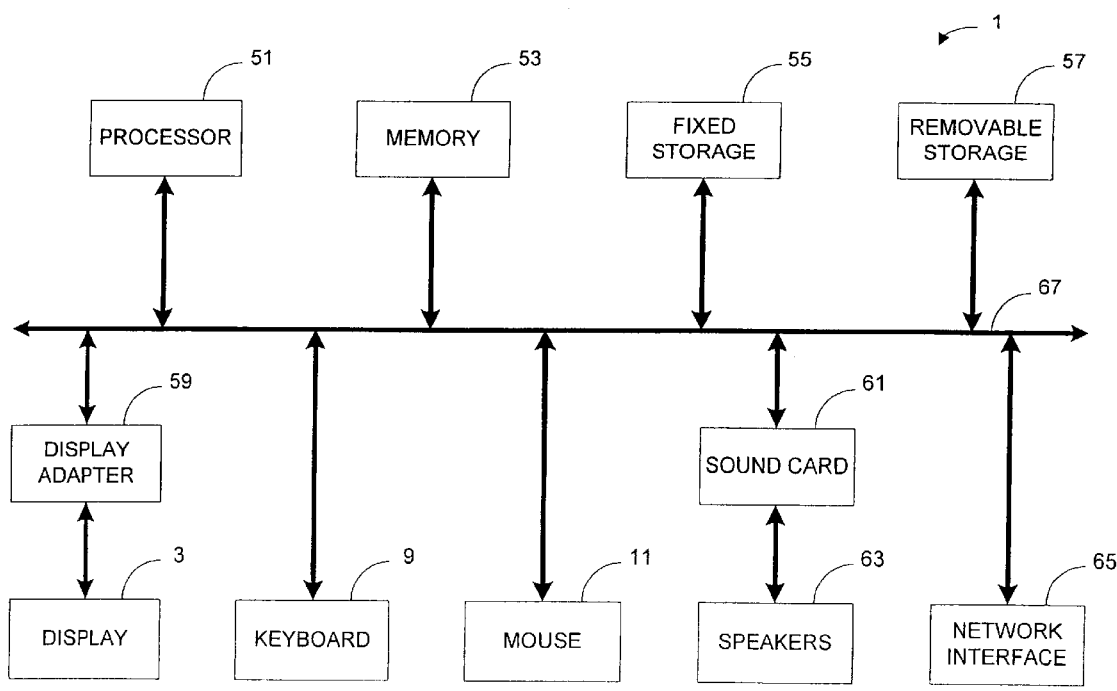
FIG. 2 illustrates a system block diagram of the computer system of FIG. 1.

FIG. 2 shows a system block diagram of computer system 1 used to execute the software of an embodiment of the invention. As in FIG. 1, computer system 1 includes monitor 3 and keyboard 9, and mouse 11. Computer system 1 further includes subsystems such as a central processor 51, system memory 53, fixed storage 55 (e.g., hard drive), removable storage 57 (e.g., CD-ROM drive), display adapter 59, sound card 61, speakers 63, and network interface 65. Other computer systems suitable for use with the invention ay include additional or fewer subsystems. For example, another computer system could include more than one processor 51 (i.e., a multi-processor system) or a cache memory.

The system bus architecture of computer system 1 is represented by arrows 67. However, these arrows are illustrative of any interconnection scheme serving to link the subsystems. For example, a local bus could be utilized to connect the central processor to the system memory and display adapter. Computer system 1 shown in FIG. 2 is but an example of a computer system suitable for use with the invention. Other computer architectures having different configurations of subsystems may also be utilized.

The present invention provides methods of aligning scanned images or image files of hybridized chips including nucleic acid probes. In a representative embodiment, the scanned image files include fluorescence data from a biological array, but the files may also represent other data such as radioactive intensity, light scattering, refractive index, conductivity, electroluminescence, or large molecule detection data. Therefore, the present invention is not limited to analyzing fluorescence measurements of hybridization but may be readily utilized to analyze other measurements of hybridization.

For purposes of illustration, the present invention is described as being part of a computer system that designs a chip mask, synthesizes the probes on the chip, labels the nucleic acids, and scans the hybridized nucleic acid probes. Such a system is fully described in U.S. Pat. No. 5,571,639 that has been incorporated by reference for all purposes. However, the present invention may be used separately from the overall system for analyzing data generated by such systems.

Figure 3:
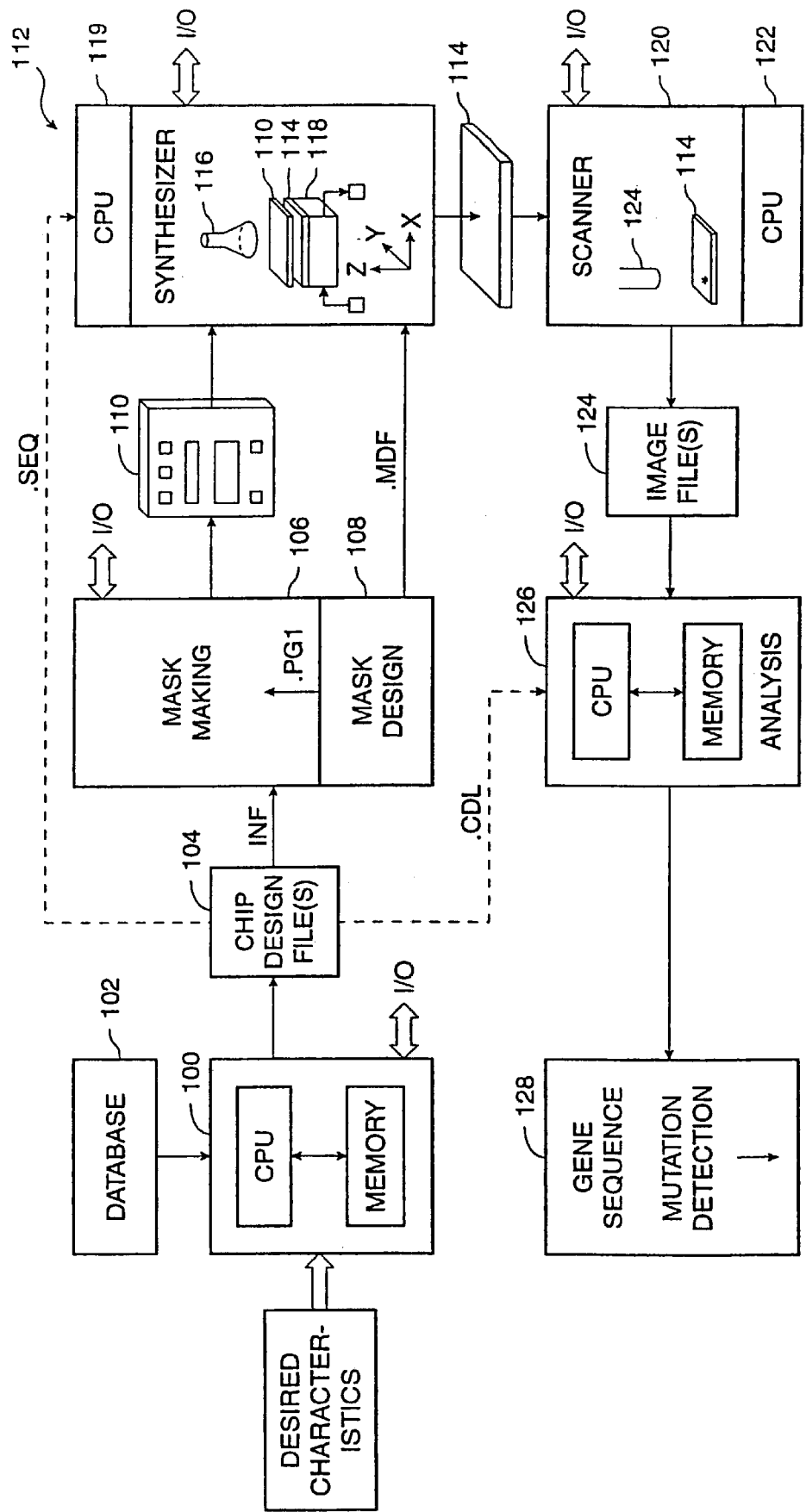
FIG. 3 illustrates an overall system for forming and analyzing arrays of biological materials such as DNA or RNA.

FIG. 3 illustrates a computerized system for forming and analyzing arrays of biological materials such as RNA or DNA. A computer 100 is used to design arrays of biological polymers such as RNA and DNA. The computer 100 may be, for example, an appropriately programmed Sun Workstation or personal computer or workstation, such as an IBM PC equivalent, including appropriate memory and a CPU as shown in FIGS. 1 and 2. The computer system 100 obtains inputs from a user regarding characteristics of a gene of interest, and other inputs regarding the desired features of the array. Optionally, the computer system may obtain information regarding a specific genetic sequence of interest from an external or internal database 102 such as GenBank. The output of the computer system 100 is a set of chip design computer files 104 in the form of, for example, a switch matrix, as described in PCT application WO 92/10092, and other associated computer files.

The chip design files are provided to a system 106 that designs the lithographic masks used in the fabrication of arrays of molecules such as DNA. The system or process 106 may include the hardware necessary to manufacture masks 110 and also the necessary computer hardware and software 108 necessary to lay the mask patterns out on the mask in an efficient manner. As with the other features in FIG. 3, such equipment may or may not be located at the same physical site but is shown together for ease of illustration in FIG. 3. The system 106 generates masks 110 or other synthesis patterns such as chrome-on-glass masks for use in the fabrication of polymer arrays.

The masks 110, as well as selected information relating to the design of the chips from system 100, are used in a synthesis system 112. Synthesis system 112 includes the necessary hardware and software used to fabricate arrays of polymers on a substrate or chip 114. For example, synthesizer 112 includes a light source 116 and a chemical flow cell 118 on which the substrate or chip 114 is placed. Mask 110 is placed between the light source and the substrate/chip, and the two are translated relative to each other at appropriate times for deprotection of selected regions of the chip. Selected chemical regents are directed through flow cell 118 for coupling to deprotected regions, as well as for washing and other operations. All operations are preferably directed by an appropriately programmed computer 119, which may or may not be the same computer as the computer(s) used in mask design and mask making.

The substrates fabricated by synthesis system 112 are optionally diced into smaller chips and exposed to marked targets. The targets may or may not be complementary to one or more of the molecules on the substrate. The targets are marked with a label such as a fluorescein label (indicated by an asterisk in FIG. 3) and placed in scanning system 120. Scanning system 120 again operates under the direction of an appropriately programmed digital computer 122, which also may or may not be the same computer as the computers used in synthesis, mask making, and mask design. The scanner 120 includes a detection device 124 such as a confocal microscope or CCD (charge-coupled device) that is used to detect the location where labeled target (*) has bound to the substrate. The output of scanner 120 is an image file(s) 124 indicating, in the case of fluorescein labeled target, the fluorescence intensity (photon counts or other related measurements, such as voltage) as a function of position on the substrate. Since higher photon counts will be observed where the labeled target has bound more strongly to the array of polymers (e.g., DNA probes on the substrate), and since the monomer sequence of the polymers on the substrate is known as a function of position, it becomes possible to determine the sequence(s) of polymer(s) on the substrate that are complementary to the target.

The image file 124 is provided as input to an analysis system 126 that incorporates the scanned image alignment techniques of the present invention. Again, the analysis system may be any one of a wide variety of computer system(s), but in a preferred embodiment the analysis system is based on a WINDOWS NT workstation or equivalent. The analysis system may analyze the image file(s) to generate appropriate output 128, such as the identity of specific mutations in a target such as DNA or RNA.

Figure 4:
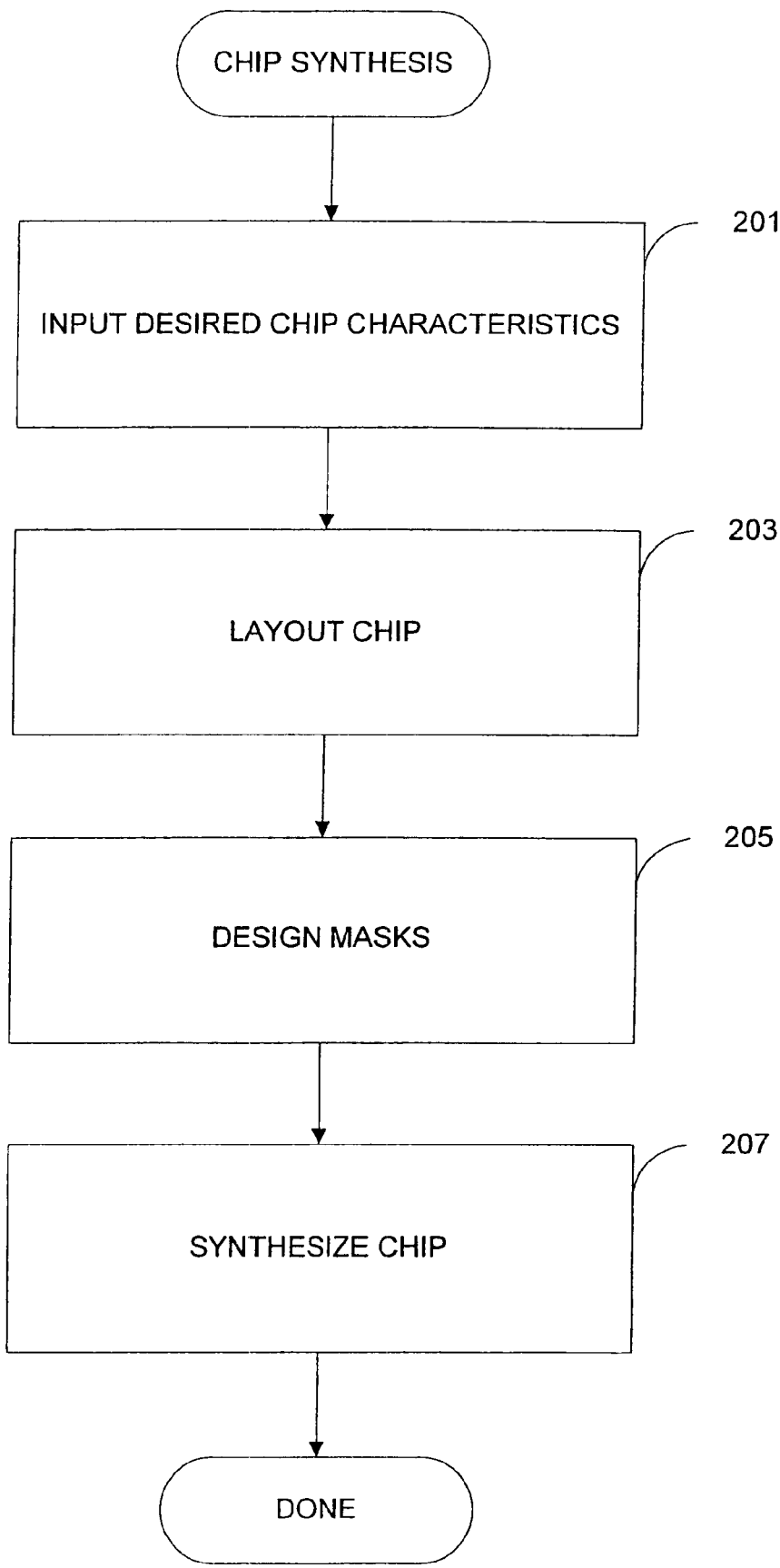
FIG. 4 is a high level flowchart of a process of synthesizing a chip.

FIG. 4 is a high level flowchart of a process of synthesizing a chip. At a step 201, the desired chip characteristics are input to the chip synthesis system. The chip characteristics may include (such as sequence checking systems) the genetic sequence(s) or targets that would be of interest. The sequences of interest may, for example, identify a virus, microorganism or individual. Additionally, the sequence of interest may provide information about genetic diseases, cancers or infectious diseases. Sequence selection may be provided via manual input of text files or may be from external sources such as GenBank. In a preferred embodiment that performs de novo sequencing of target nucleic acids, this steps is not necessary as the chip includes all the possible n-mer probes (where represents the length of the nucleic acid probe).

For de novo sequencing, a chip may be synthesized to include cells containing all he possible probes of a specific length. For example, a chip may be synthesized that includes all the possible 8-mer DNA probes. Such a chip would have 65,536 cells (4*4*4*4*4*4*4*4), with each cell corresponding to a particular probe. A chip may also include other probes including all the probes of other lengths.

At a step 203 the system determines which probes would be desirable on the chip, and provides an appropriate "layout" on the chip for the probes. The layout implements desired characteristics such as an arrangement on the chip that permits "reading" of genetic sequence and/or minimization of edge effects, ease of synthesis, and the like.

The masks for the chip synthesis are designed at a step 205. The masks are designed according to the desired chip characteristics and layout. At a step 207, the system synthesizes the DNA or other polymer chips. Software controls, among other things, the relative translation of the substrate and mask, the flow of the desired reagents through a flow cell, the synthesis temperature of the flow cell, and other parameters.

Figure 5:
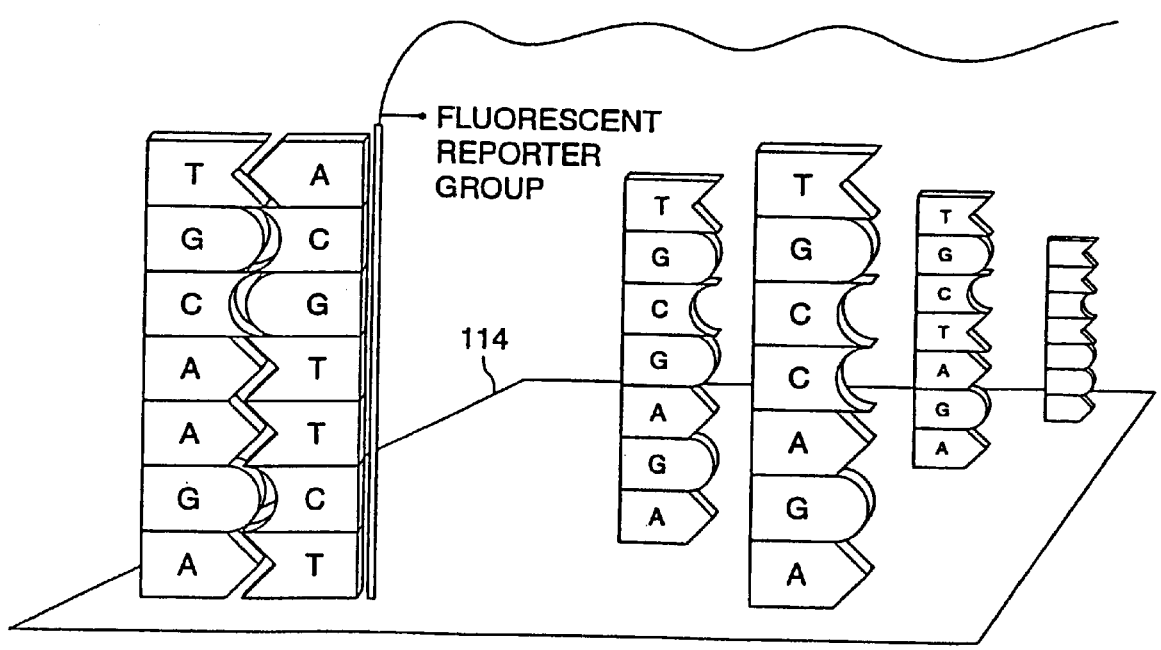
FIG. 5 illustrates conceptually the binding of probes on chips.

FIG. 5 illustrates the binding of a particular target DNA to an array of DNA probes 114. As shown in this simple example, the following probes are formed in the array:

```
3'-AGAACGT
  AGACCGT
  AGAGCGT
  AGATCGT
     .
     .
     .
```

As shown, when the fluorescein-labeled (or otherwise marked) target 5'-TCTTGCA is exposed to the array, it is complementary only to the probe 3'-AGAACGT, and fluorescein will be primarily found on the surface of the chip where 3'-AGAACGT is located. The chip contains cells that include multiple copies of a particular probe. Thus, the image file will contain fluorescence intensities, one for each probe (or cell). By analyzing the fluorescence intensities associated with a specific probe, it becomes possible to extract sequence information from such arrays using the methods of the invention disclosed herein.

For ease of reference, one may call bases by assigning the bases the following codes:

| Code | Group | Meaning |
|---|---|---|
| A | A | Adenine |
| C | C | Cytosine |
| G | G | Guanine |
| T | T(U) | Thymine (Uracil) |
| M | A or C | aMino |
| R | A or G | puRine |
| W | A or T(U) | Weak interaction (2 H bonds) |
| Y | C or T(U) | pYrimidine |
| S | C or G | Strong interaction (3 H bonds) |
| K | G or T(U) | Keto |
| V | A, C or G | not T(U) |
| H | A, C or T(U) | not G |
| D | A, G or T(U) | not C |
| B | C, G or T(U) | not A |
| N | A, C, G or T(U) | Insufficient intensity to call |
| X | A, C, G, or T(U) | Insufficient discrimination to call |

Most of the codes conform to the IUPAC standard. However, code N has been redefined and code X has been added.

Scanned Image Alignment

Figure 6:
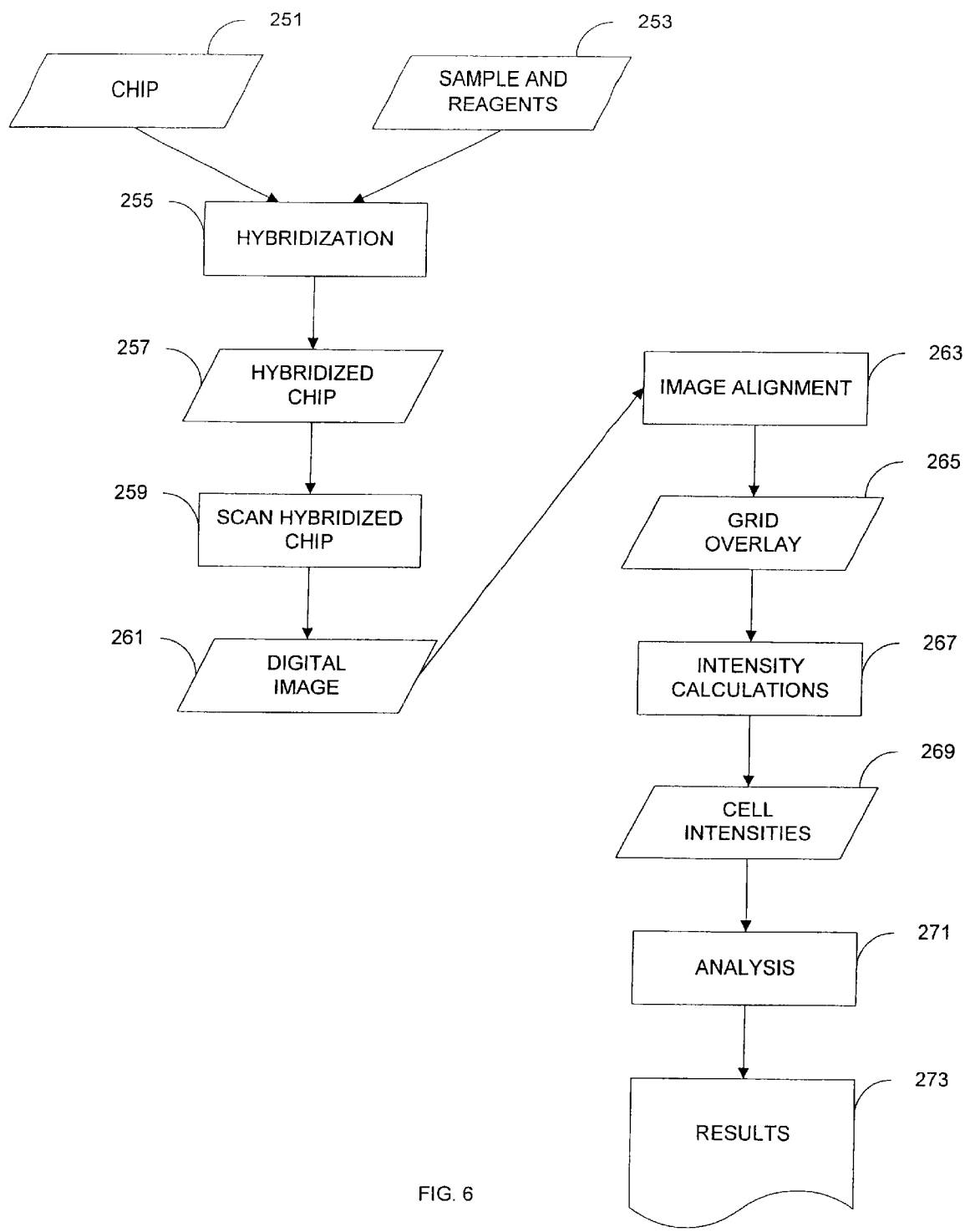
FIG. 6 illustrates a flowchart of how a chip is hybridized and analyzed to produce experimental results.

Before the scanned image alignment of the invention are discussed, it may be helpful to provide an overview of the overall process in one embodiment. FIG. 6 illustrates a flowchart of a process of how a chip is hybridized and analyzed to produce experimental results. A chip 251 having attached nucleic acid sequences (or probes) is combined with a sample nucleic acid sequence (e.g., labeled fragments of the sample) and reagents in a hybridization step 255. The hybridization step produces a hybridized chip 257.

The hybridized chip is scanned at a step 259. For example, the hybridized chip may be laser scanned to detect where fluorescein-labeled sample fragments have hybridized to the chip. Numerous techniques may be utilized to label the sample fragments and the scanning process will typically be performed according to the type of label utilized. The scanning step produces a digital image of the chip.

In preferred embodiments, the scanned image of the chip includes varying fluorescent intensities that correspond to the hybridization intensity or affinity of the sample to the probes in a cell. In order to achieve more accurate results, it is beneficial to identify the pixels that belong to each cell on the chip. At an image alignment step 263, the scanned image is aligned so that the pixels that correspond to each cell can be identified. Optionally, the image alignment step includes the alignment of a grid over the scanned image (see FIG. 7B).

At a step 267, the analysis system analyzes the scanned image to calculate the relative hybridization intensities for each cell of interest on the chip. For example, the hybridization intensity for a cell, and therefore the relative hybridization affinity between the probe of the cell and the sample sequence, may be calculated as the mean of the pixel values within the cell. The pixel values may correspond to photon counts from the labeled hybridized sample fragments.

The cell intensities may be stored as a cell intensity file 269. In preferred embodiments, the cell intensity file includes a list of cell intensities for the cells. At an analysis step 271, the analysis system may analyze the cell intensity file and chip characteristics to generate results 273. The chip characteristics may be utilized to identify the probes that have been synthesized at each cell on the chip. By analyzing both the sequence of the probes and their hybridization intensities from the cell intensity file, the system is able to extract sequence information such as the location of mutations, deletions or insertions, or the sequence of the sample nucleic acid. Accordingly, the results may include sequence information, graphs of the hybridization intensities of probe(s), graphs of the differences between sequences, and the like. See U.S. patent application Ser. No. 08/327,525, which is hereby incorporated by reference for all purposes.

In order to align the scanned image, the invention provides a pattern in the scanned image that will be convolved into a recognizable pattern. In preferred embodiments, the pattern in the scanned image is a checkerboard pattern that is generated by synthesizing alternating cells that include probes that are complementary to a control nucleic acid sequence. The control nucleic acid sequence may be a known sequence that is labeled and hybridized to the chip for the purpose of aligning the scanned image. Additionally, the brightness of the cells complementary to the control nucleic acid sequence may be utilized as a baseline or for comparison to other intensities.

Figure 7A:
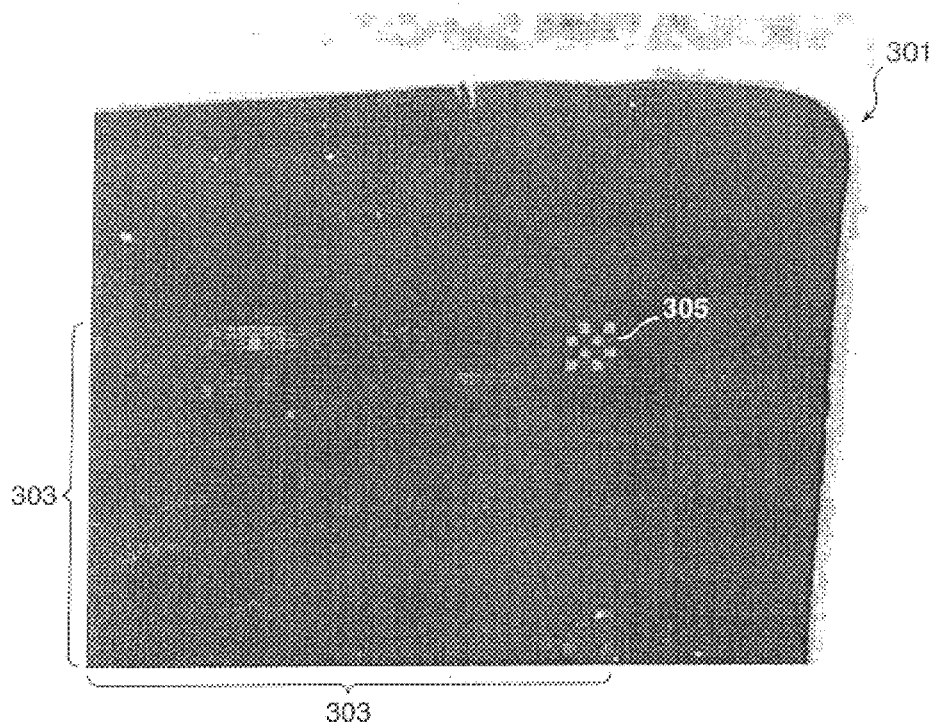
FIG. 7A shows a checkerboard pattern in a scanned image and FIG. 7B shows a grid that has been aligned over the scanned image to show the individual cells on the chip.

As an example, FIG. 7A shows a checkerboard pattern in a hybridized chip. A scanned image 301 of a hybridized chip includes an active area 303 where the probes were synthesized. At the corner of the active area is a pattern 305 that is a checkerboard pattern. Typically, the pattern appears at each corner of the active area of the scanned image. Although the pattern is shown as being a checkerboard pattern, in other embodiments the pattern is a circle, square, plus sign, or any other pattern.

Figure 7B:
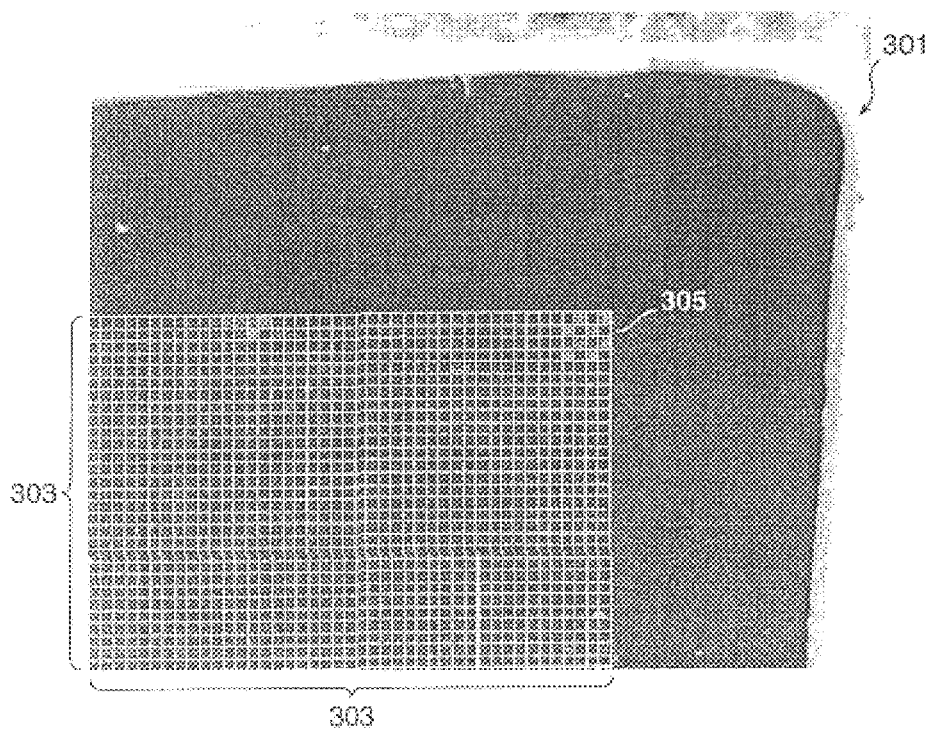

With regard to FIG. 6, it was stated that a grid may optionally be placed over the scanned image to show or delineate the individual cells of the chip. FIG. 7B shows a grid that has been aligned over the scanned image of FIG. 7A to show the individual cells of the chip. As shown, a grid 307 has been placed over active area 303 of hybridized chip 301.

Figure 8:
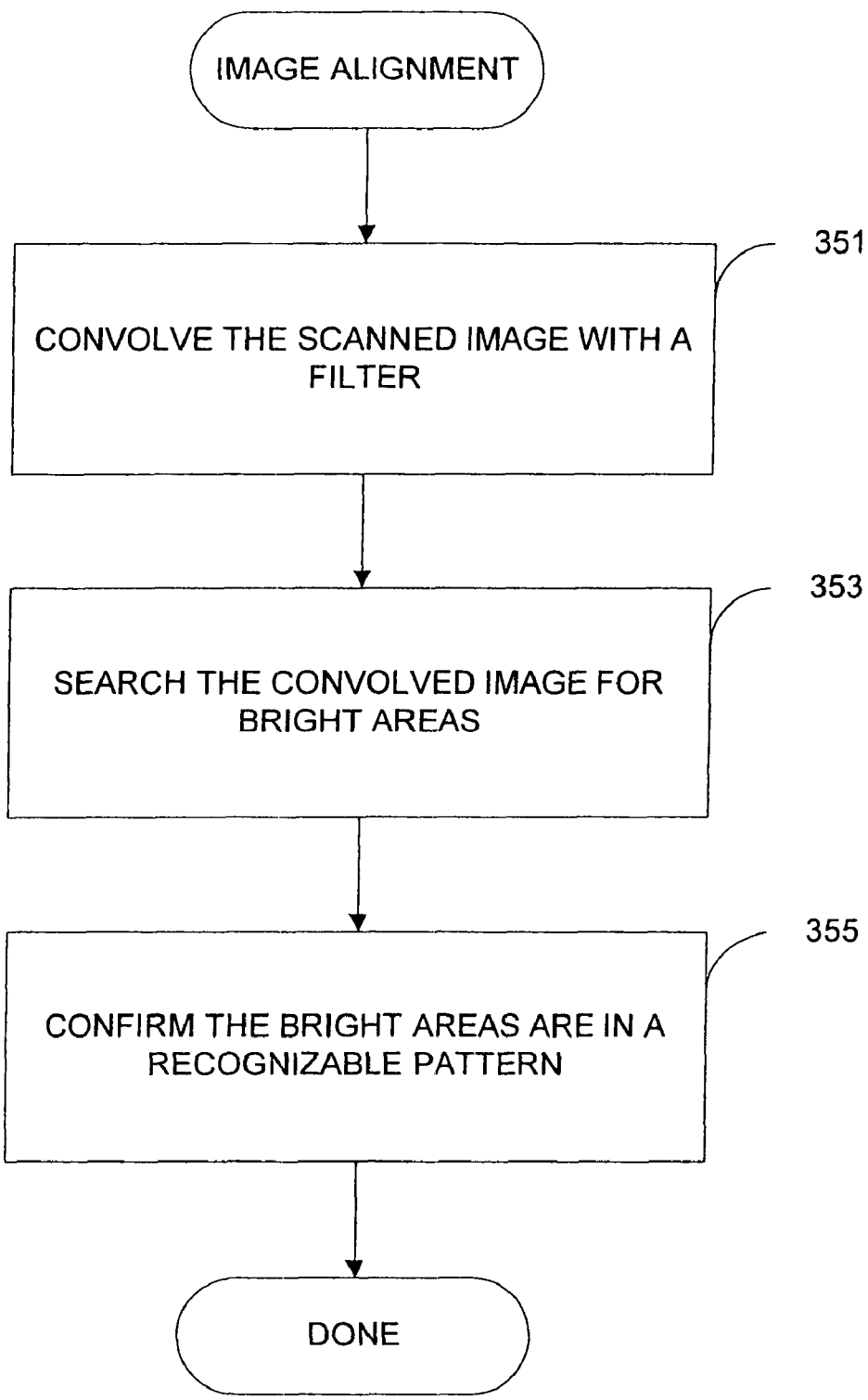
FIG. 8 illustrates a flowchart of a process of image alignment.

FIG. 8 illustrates a flowchart of a process of image alignment. The flowchart shows detail for step 263 of FIG. 6. At a step 351, the scanned image is convolved with a filter.

The filter is typically a software filter that convolves the scanned image into a convolved image. When the scanned image is convolved, a pattern in the scanned image is convolved into a recognizable pattern. The position of the recognizable pattern in the convolved image may be utilized to align the scanned image, such as by placing a grid over the image.

At a step 353, the convolved image is searched for bright areas. When the scanned image is convolved, the pattern(s) in the scanned image will be convolved into a recognizable pattern or patterns of bright areas. Accordingly, once bright areas are identified in the convolved image, the system confirms that the bright areas are in the expected recognizable pattern (e.g., a grid pattern) at a step 355.

Figure 9A:
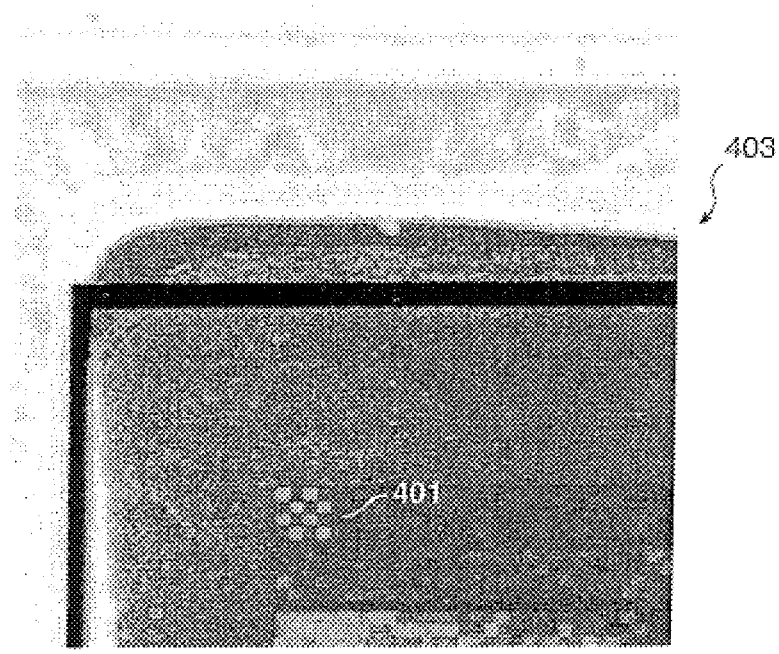
FIG. 9A shows a checkerboard pattern in a scanned image and FIG. 9B shows a convolved image of FIG. 9A with a grid pattern that was generated by the checkerboard pattern.
Figure 9B:
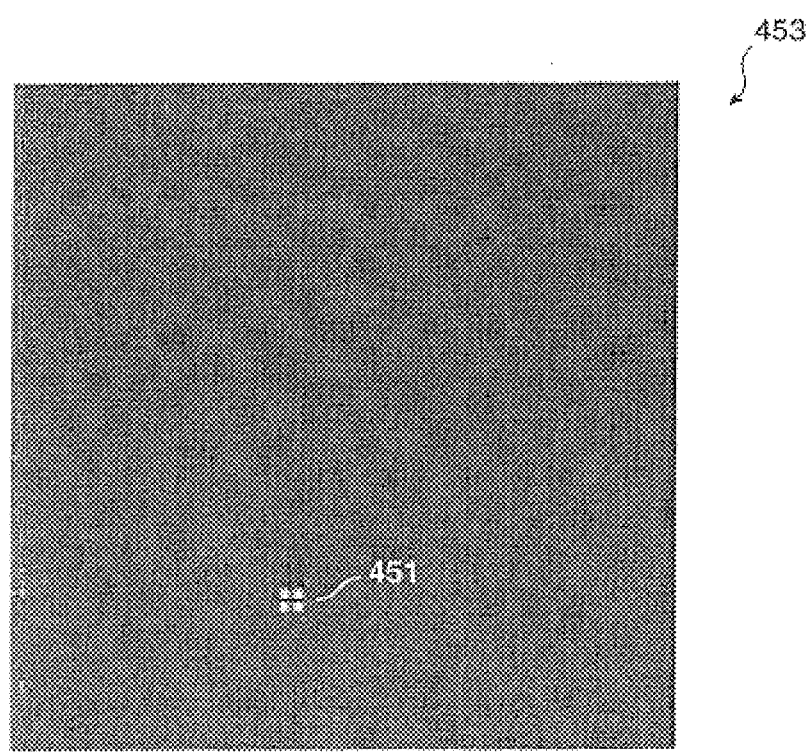

In order to better understand what is meant by the different patterns, FIG. 9A shows a checkerboard pattern 401 in a scanned image 403. FIG. 9B shows a recognizable pattern 451 in convolved image 453. The convolved image was generated from the scanned image of FIG. 9A. As shown, recognizable pattern 41 in this embodiment is a grid pattern that was generated by the checkerboard pattern when it was convolved with a filter. Additionally, it should be noted that the filter acted to remove the other pixel intensities so that the convolved image only includes the recognizable pattern. By removing pixel intensities that are not part of the pattern in the scanned image, it is easier to align the scanned image.

Figure 10:
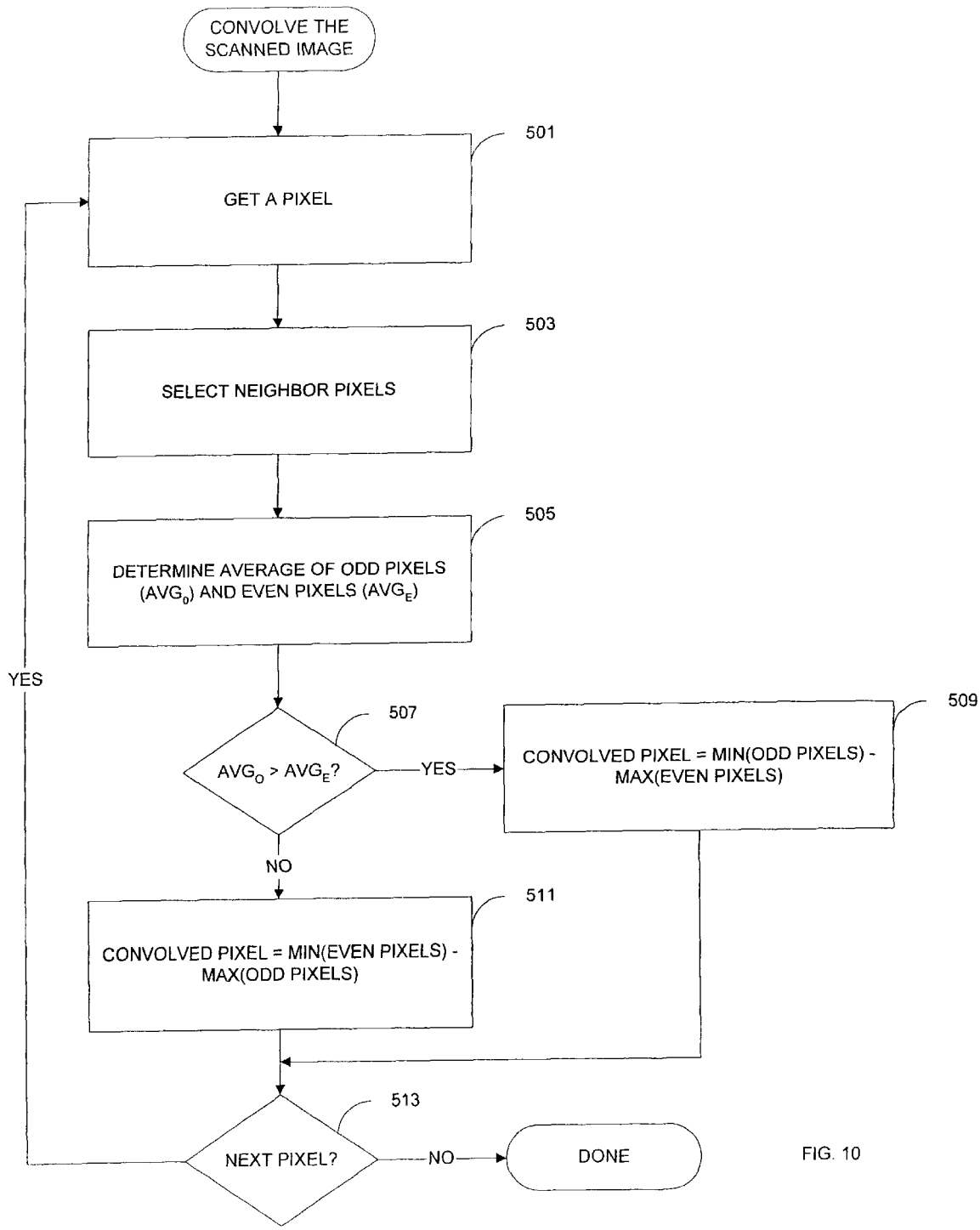
FIG. 10 illustrates a flowchart of a process of convolving the scanned image.

FIG. 10 illustrates a flowchart of a process of convolving the scanned image. The flowchart illustrates a process that may be performed at step 351 of FIG. 8. At a step 501, a pixel is selected. For simplicity, we will assume that the process selects pixels of the scanned image from left to right and top to bottom. Of course, the order that the pixels are analyzed may be varied.

Figure 11:
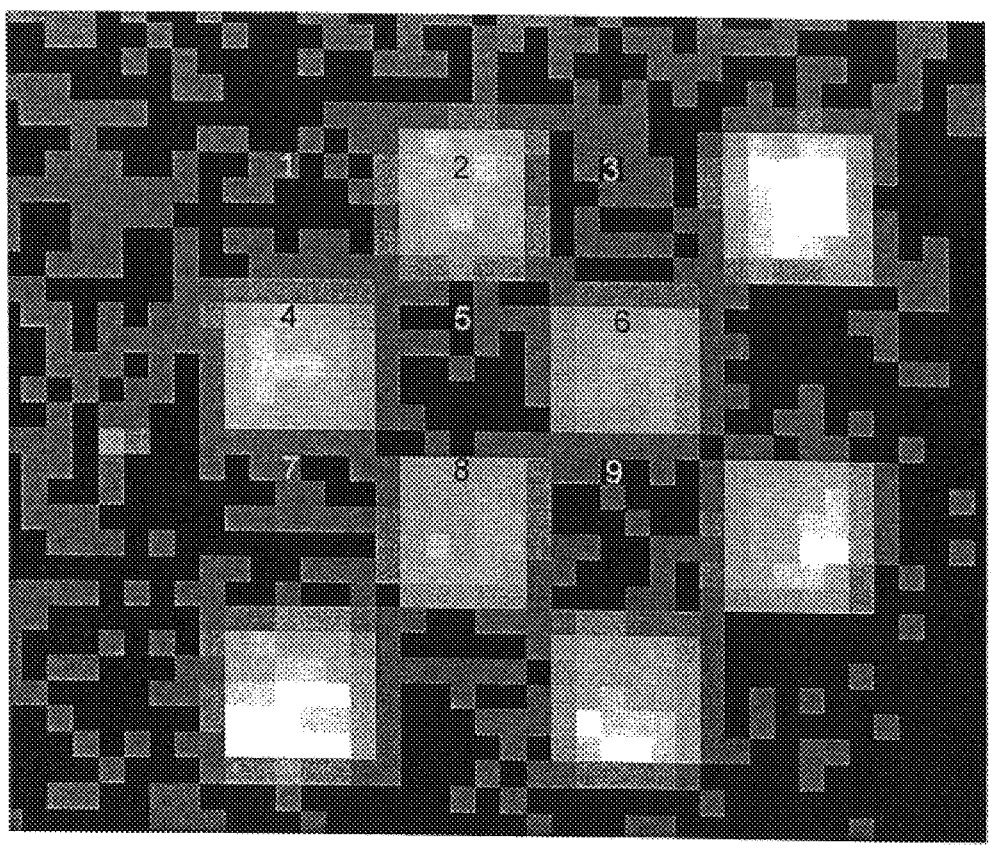
FIG. 11 shows neighbor pixels that may be analyzed to produce a convolved pixel in the convolved image.

Once a pixel selected, neighbor pixels may then be selected at a step 503. By neighbor pixels, it is meant pixels that the pixels are near, but not necessarily adjacent to a pixel. For example, FIG. 11 shows neighbor pixels that may be analyzed to produce a convolved pixel in a convolved image. As shown in FIG. 11, there are 9 pixels labeled 1–9. In a preferred embodiment, pixel 1 is the pixel retrieved at step 501 and the neighbor pixels retrieved at step 503 are pixels 2–9. Of course, any number or location of different neighbor pixels may be utilized.

At a step 505, the average of the odd pixels and the average of the even pixels is determined. Referring again to FIG. 11, the intensities of pixels 1, 3, 5, 7, and 9 may be averaged to produce the average of the odd pixels ($AVG_O$). Similarly, the intensities of pixels 2, 4, 6, and 8 may be averaged to produce the average of the odd pixels ($AVG_E$). Thus, the odd pixels may be pixels that have an odd number designation and the even pixels may be pixels that have an even number designation.

Pixel 1 is convolved into a convolved pixel in a convolved image by determining if the average of the odd pixels is greater than the average of the even pixels at a step 507. If the average of the odd pixels is greater, the convolved pixel is set equal to the intensity of the minimum of the odd pixels minus the intensity of the maximum of the even pixels at a step 509. Otherwise, the convolved pixel is set equal to the intensity of the minimum of the even pixels minus the intensity of the maximum of the odd pixels at a step 511.

Conceptually, the neighbor pixels may be thought of as being filtered, such as by a software filter in preferred embodiments. With the filter, the system is searching for a checkerboard pattern where all the odd pixels are either darker or lighter than the even pixels. Accordingly, averages of the odd and even pixels are calculated at step 505. Step 507 acts to determine if the pixels likely reflect a checkerboard pattern where the odd pixels, and therefore squares, are light (e.g., high intensity) or dark (e.g., low intensity). If the odd pixels likely reflect a checkerboard pattern where the odd pixels are light, step 509 sets the convolved pixel to the difference between selected odd and even pixels, where the selected odd pixel is the minimum of the odd pixels and the selected even pixel is the maximum of the even pixels. Step 511 is similar but reversed.

Therefore, at step 509, if all the odd pixels are much brighter than all the even pixels, the difference will be a larger value. Hence, the convolved pixel will be relatively bright (e.g., high intensity). The convolved pixel will also be relatively bright if all the even pixels are much brighter than all the odd pixels at step 511. However, if the difference at step 509 or 511 is very small (or negative), the convolved pixel will be set to a relatively dark intensity. Convolved pixels with negative pixel values may be set to a zero in preferred embodiments. In short, if the filter finds a checkerboard pattern, the convolved pixel will be bright and if the filter finds a relatively random pattern, the convolved pixel will be dark (thus, filtering out "noise" that is not the desired pattern).

Figure 12A:
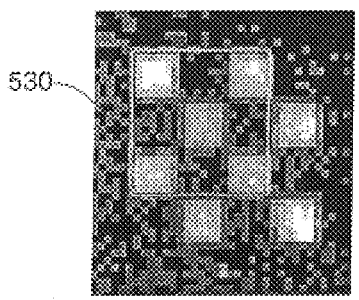
FIGS. 12A–12D show how the filter may be moved over the scanned image to produce the convolved image.
Figure 12B:
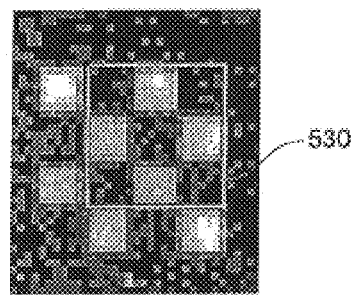
Figure 12C:
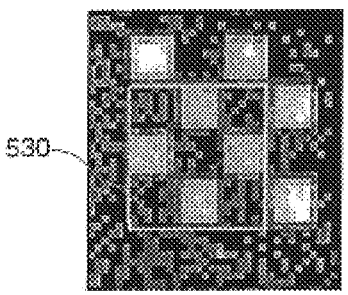
Figure 12D:
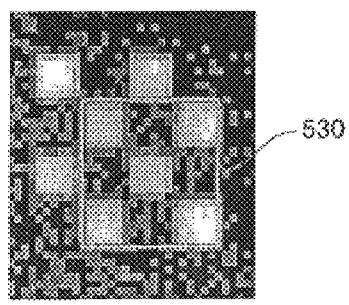

The recognizable pattern in FIG. 9B, which is a grid pattern, was generated by the software filter of FIG. 10. In order to better see how the recognizable pattern was generated, FIGS. 12A–D show how the filter may be moved over the checkerboard to produce a grid pattern in the convolved image. As the filter is convolved over the pattern in the scanned image shown in a square 530 in FIG. 12A, a bright square will be generated in the convolved image since a checkerboard pattern will be found. Similarly, a bright square will be generated in the convolved image when the filter is over the pattern in square 530 of FIG. 12B. Of course, the checkerboard patterns in square 530 of FIGS. 12A and 12B are reversed, but both will produce a bright square in the convolved image as described above in reference to FIG. 10. FIGS. 12C and 12D will also produce two bright squares. Therefore, a 2×2 bright square grid pattern is generated as shown in FIG. 9B.

Additionally, as the software filter of FIG. 10 acts to filter out signals that are not the desired pattern, the recognizable pattern (e.g., a grid pattern) is easier to identify. The recognizable patterns in the convolved image are utilized to align the scanned image. Returning now to FIG. 10, after a selected pixel is convolved into a convolved pixel by the filter, it is determined if there is another pixel to process in the scanned image at a step 513.

The following shows how well an embodiment of the invention aligned scanned images of hybridized chips:

|  | Previous method | With filter convolution |
| --- | --- | --- |
| Perfect alignment | 0% | 4% |
| 1 pixel off | 8% | 96% |
| 2 or more pixels off | 20% | 0% |
| 1 or more cells off | 12% | 0% |
| unable to align | 60% | 0% |

The previous method was to analyze the scanned image (unfiltered) to locate bright areas or spots in a checkerboard pattern. As shown, an embodiment of the invention was able to dramatically increase the accuracy of scanned image alignment.

Refined Grid Alignment

Figure 13:
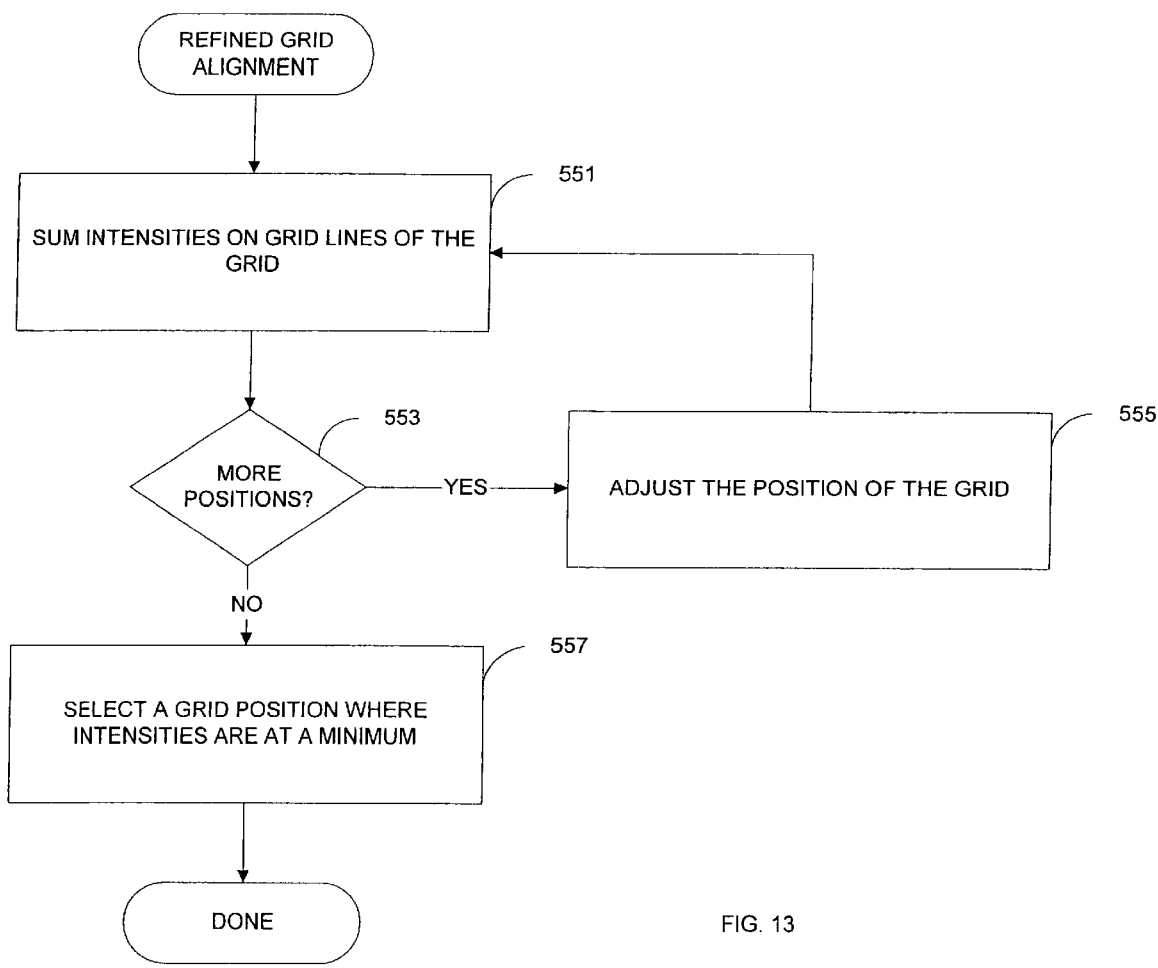
FIG. 13 illustrates a flowchart of a process of refining the grid alignment over the scanned image.

In preferred embodiments, refined image alignment may be performed to further increase the accuracy of the scanned image alignment. FIG. 13 illustrates a flowchart of a process of refining grid alignment over a scanned image. Thus, for example, once the above-described process has been performed to align the scanned image, the process in FIG. 13 may be utilized to refine the alignment.

Figure 14:
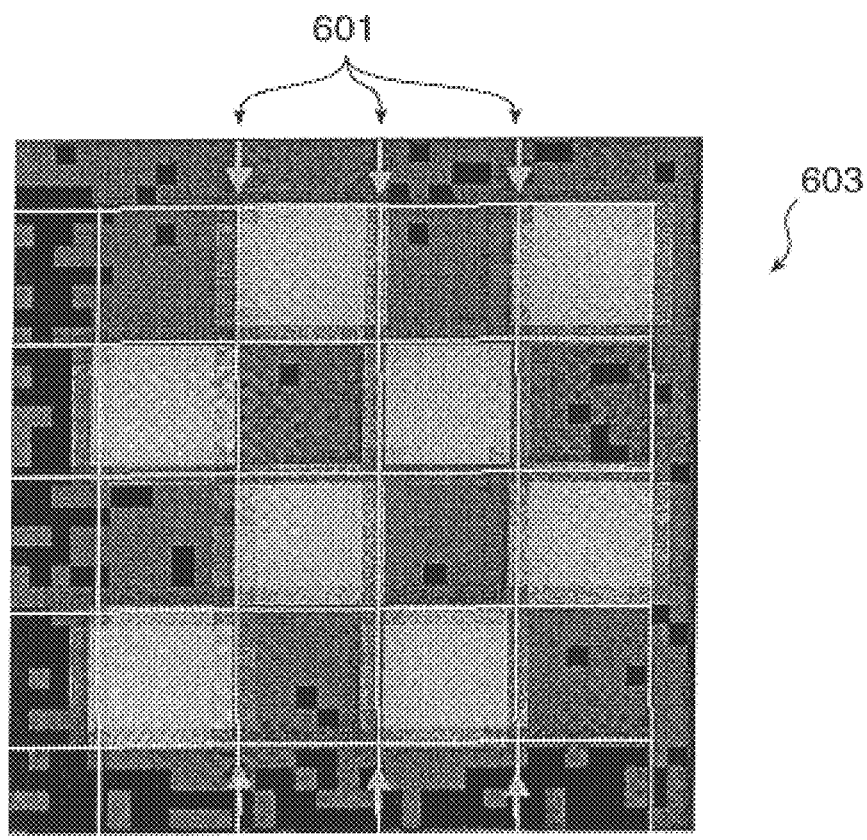
FIG. 14 shows the grid lines in the scanned image that may be analyzed to refine the grid alignment.

At a step 551, pixel intensities on grid lines in the grid are summed. For example, the intensities of the grid in a vertical direction in the checkerboard pattern in the scanned image may be summed. FIG. 14 shows the grid lines in the scanned image that may be analyzed to refine the grid alignment. As shown, the pixel intensities of vertical lines 601 of a checkerboard pattern 603 may be summed and stored.

Then, at a step 553, the system may determine if there are more positions of the grid to analyze. If there are, the position of the grid may be adjusted at a step 555. Therefore, the grid may be moved left and right by one or more pixels before the intensities are summed along grid lines at step 551. Once all the positions of the grid have been analyzed, the system selects a grid position where pixel intensities (e.g., the sum calculated at step 551) are at a minimum. Therefore, if the pixel intensities for grid lines are lower at another position, the grid is adjusted accordingly. This refinement will work well if the cells are typically separated by a darker area or line.

Although the process in FIG. 13 was described for grid lines in the vertical direction, preferred embodiments also perform the same grid alignment for the horizontal direction. The distance that the grid is able to be moved for refinement may be limited. For example, the grid may be limited to movement of one-third a cell size.

The following shows how well an embodiment of the invention aligned scanned images of hybridized chips utilizing the refined grid alignment:

|  | Previous method | With refined grid alignment |
| --- | --- | --- |
| Perfect alignment | 0% | 64% |
| 1 pixel off | 8% | 36% |
| 2 or more pixels off | 20% | 0% |
| 1 or more cells off | 12% | 0% |
| unable to align | 60% | 0% |

Once again, the previous method was to analyze the scanned image (unfiltered) to locate bright areas or spots in a checkerboard pattern. As shown, an embodiment of the invention was able to dramatically increase the accuracy of scanned image alignment. Furthermore, refining grid alignment increased the percentage of scanned images that were perfectly aligned with the invention from 4% to 64%. Therefore, performing a refinement of grid alignment can significantly increase the accuracy of the grid alignment.

Conclusion

While the above is a complete description of preferred embodiments of the invention, various alternatives, modifications, and equivalents may be used. It should be evident that the invention is equally applicable by making appropriate modifications to the embodiments described above. For example, the invention has been described in reference to a checkerboard pattern in the scanned image. However, the invention is not limited to any one pattern and may be advantageously applied to other patterns including those described herein. Therefore, the above description should not be taken as limiting the scope of the invention that is defined by the metes and bounds of the appended claims along with their full scope of equivalents.

Software listing of the algorithm:
```
///////////////////////////////////////////////////////////
//      CheckerFilt
//      purpose
//           perform a checker-board kernel filter on the image.
//      input
//           cellWidth, cellHeight, size of the cell
//           *img, the #of rows and columns in the image and the image data
//      output
//           *img, the image is filtered in place
void CheckerFilt(int cellWidth, int cellHeight, IMAGE *img)
{
    int row,col,rowBegin,nRows,nCols,colBegin,rowEndFilter,colEndFilter,imgOffset;
    int oddAvg,evenAvg,oddMin,oddMax,evenMin,evenMax;
    int temp;
    PIX_T *e1=NULL,*e2=NULL,*e3=NULL,*e4=NULL,*e5=NULL,*e6=NULL,*e7=NULL,*e8=NULL,*e9=NULL;
    //
    // Determine the range of rows and columns to filter
    rowBegin=0;
    colBegin=0;
    nRows=img->rows;
    nCols=img->cols;
    rowEndFilter=nRows-1-2*cellHeight;
    colEndFilter=nCols-1-2*cellWidth;
    //For each row
    for (row=rowBegin;row<=rowEndFilter;row++)
    {
        //Initialize the filter's pointers
        // e1 e2 e3
        // e4 e5 e6
        // e7 e8 e9
        //
        Set3x3Pointers(img, row, cellWidth, cellHeight, &e1, &e2, &e3, &e4, &e5, &e6, &e7, &e8, &e9);
        // walk the row, doing the filter
        for(col=colBegin;col<=colEndFilter;col++)
        {
            // Avg1 = Average pixels 1, 3, 5, 7, 9
            // Avg2 = Average pixels 2, 4, 6, 8
            oddAvg = (e1[col] + e3[col] + e5[col + e7[col] + e9[col])/5;
            evenAvg = (e2[col] + e4[col] + e6[col + e8[col])/4;
            //   If avgOdd > avg Even
            //      Then the area is bright and
            //         NewPixel = min(v1,v3,v5,v7,v9) - max(v2,v4,v6,v8)
            //      Else the area is dark and
            //         NewPixel = min(v2,v4,v6,v8) - max(v1,v3,v5,v7,v9)
            //
            if (oddAvg > evenAvg)
            {
                oddMin=MIN(e1[col],MIN(e3[col], MIN(e5[col], MIN(e7[col], e9[col]))));
                evenMax = MAX(e2[col],MAX(e4[col], MAX(e6[col], e8[col])));
                e1[col]= MAX(0,oddMin-evenMax);
                temp=e1[col];
                if(temp >0)
                    temp=e1[col];
            }
            else
            {
                evenMin = MIN(e2[col],MIN(e4[col], MIN(e6[col], e8[col])));
                oddMax=MAX(e1[col],MAXe3[col], MAX(e5[col], MAX(e7[col], e9[col]))));
                e1[col] = MAX(0,evenMin - oddMax);
                temp=e1[col];
                if(temp >0)
                    temp=e1[col];
            }
        }
    }
    //Set the border pixels, which are not filtered, to zero.
    for(row=0;row<nRows;row++)
    {
        imgOffset=row* (img->cols);
        e1=img->image+imgOffset;
        if(row<rowEndFilter)
            colBegin=colEndFilter;
        else
            colBegin=0;
        for(col=colBegin;col<nCols;col++)
            e1[col]=0;
    }
    return;
```

-continued

```
}
////////////////////////////////////////////////////////////////
//    Set3x3Pointers
//    purpose
//        initialize pointers that will be used when walking the kernel along
//        a row of image data.
//    input
//        *img: image struct contains number of rows and columns in the image
//        row: the row of the image on which we are applying the kernel
//        cellWidth, cellHeight: size of the cell which implies the size of the kernel
//
//    output
//        e1..e9: pointers to the 9 pixels that will be used for kernel calculations
//
void Set3x3Pointers(IMAGE *img,int row, int cellWidth, int cellHeight,
   PIX_T **e1,PIX_T **e2,PIX_T **e3,PIX_T **e4,PIX_T **e5,PIX_T **e6,
PIX_T **e7,PIX_T **e8,PIX_T **e9,PIX_T
{
    PIX_T *p1=NULL,*p2=NULL,*p3=NULL;
    int imgOffset;
    int cellWidthTimes2=cellWidth*2;
    int nCols=img->cols;
    imgOffset=row*(img->cols);
    p1=img->image+imgOffset;
    p2=p1+nCols*cellHeight;
    p3=p1+nCols*2*cellHeight;
    *e1 = p1; *e2 = p1+cellWidth; *e3 = p1+cellWidthTimes2; /* SET THE POINTERS FOR THE 3 ROWS */
    *e4 = p2; *e5 = p2+cellWidth; *e6 = p2+cellWidthTimes2; /* (WHOSE POINTERS ROTATE) */
    *e7 = p3; *e8 = p3+cellWidth; *e9 = p3+cellWidthTimes2;
}
```

What is claimed is:

1. A method of aligning images, comprises:
   synthesizing a chip having attached nucleic acid sequences, the chip including a first pattern of nucleic acid sequences;
   hybridizing labeled nucleic acid sequences to nucleic acid sequences on the chip;
   scanning the hybridized chip to produce a scanned image;
   convolving the scanned image with a filter, the filter convolving the first pattern into a second pattern in a convolved image; and
   aligning the scanned image to an image of the chip according to a position of the second pattern in the convolved image.

2. The method of claim 1, wherein convolving the scanned image with a filter comprises setting a convolved pixel to a difference in intensity between an odd pixel and an even pixel of the first pattern.

3. The method of claim 2, wherein the odd pixel has the lowest intensity of the odd pixels and the even pixel has the highest intensity of the even pixels, if the average intensity of the odd pixels is greater than the average intensity of the even pixels.

4. The method of claim 2, wherein the odd pixel has the highest intensity of the odd pixels and the even pixel has the lowest intensity of the even pixels, if the average intensity of the odd pixels is not greater than the average intensity of the even pixels.

5. The method of claim 1, wherein the first pattern is a checkerboard pattern.

6. The method of claim 5, wherein the labeled nucleic acid sequences include control nucleic acid sequences that hybridize to alternating squares in the checkerboard pattern.

7. The method of claim 1, wherein the second pattern is a grid pattern.

8. The method of claim 1, wherein aligning the scanned image comprises aligning a grid over the scanned image.

9. The method of claim 8, further comprising adjusting the position of the grid to minimize a sum of the intensities of pixels along a direction in the grid.

10. The method of claim 1, wherein the scanned image includes multiple copies of the first pattern.

11. The method of claim 10, wherein the scanned image is a rectangle with a copy of the first pattern near each corner.

12. A computer program product that aligns images, comprising:
    computer code that receives as input a scanned image of a chip having attached nucleic acid sequences to which labeled nucleic acid sequences are hybridized, the chip including a first pattern of nucleic acid sequences;
    computer code that convolves the scanned image with a filter, the filter convolving the first pattern into a second pattern in a convolved image;
    computer code that aligns an image of the scanned image to the chip according to a position of the second pattern in the convolved image; and
    a computer readable medium that stores the computer codes.

13. The computer program product of claim 12, wherein the computer readable medium is a CD-ROM, floppy disk, tape, flash memory, system memory, hard drive, and a data signal embodied in a carrier wave.

14. The computer program product of claim 12, wherein convolving the scanned image with a filter comprises setting a convolved pixel to a difference in intensity between an odd pixel and an even pixel of the first pattern.

15. The computer program product of claim 14, wherein the odd pixel has the lowest intensity of the odd pixels and the even pixel has the highest intensity of the even pixels, if the average intensity of the odd pixels is greater than the average intensity of the even pixels.

16. The computer program product of claim 14, wherein the odd pixel has the highest intensity of the odd pixels and the even pixel has the lowest intensity of the even pixels, if the average intensity of the odd pixels is not greater than the average intensity of the even pixels.

17. The computer program product of claim 12, wherein the first pattern is a checkerboard pattern.

18. The computer program product of claim 17, wherein the labeled nucleic acid sequences include control nucleic acid sequences that hybridize to alternating squares in the checkerboard pattern.

19. The computer program product of claim 12, wherein the second pattern is a grid pattern.

20. The computer program product of claim 12, wherein aligning die scanned image comprises aligning a grid over the scanned image.

21. The computer program product of claim 20, further comprising adjusting the position of the grid to minimize a sum of the intensities of pixels along a direction in the grid.

22. The computer program product of claim 12, wherein the scanned image includes multiple copies of the first pattern.

23. The computer program product of claim 22, wherein the scanned image is a rectangle with a copy of the first pattern near each corner.

* * * * *